United States Patent [19]
Burke

[11] Patent Number: 5,359,137
[45] Date of Patent: Oct. 25, 1994

[54] PREPARATION OF ADIPIC ACID FROM LACTONES

[75] Inventor: Patrick M. Burke, Wilmington, Del.

[73] Assignee: E. I. Du Pont de Nemours and Company, Wilmington, Del.

[21] Appl. No.: 343,421

[22] Filed: Apr. 26, 1989

[51] Int. Cl.$^5$ ............................................. C07C 51/14
[52] U.S. Cl. .................................. 562/517; 562/590; 562/522
[58] Field of Search ................................. 562/517, 590

[56] References Cited

U.S. PATENT DOCUMENTS 4,622,423 11/1986 Burke .................................. 562/522
4,788,333 11/1988 Burke .................................. 562/517

FOREIGN PATENT DOCUMENTS 54-92913 7/1979 Japan ..................................... 562/517
55-51037 4/1980 Japan .

OTHER PUBLICATIONS

Sado et al., "Preparation of Dicarboxlic Acids from Lactone", Chem. Abst. 94:1742245q, (1980).
Sado et al., Chemical Abstracts, 91:210906e.

*Primary Examiner*—Arthur C. Prescott

[57] ABSTRACT

Conversion of certain lactones by reaction with carbon monoxide and water, in the presence of a homogeneous rhodium catalyst and an iodide or bromide promoter, to produce adipic acid.

14 Claims, 1 Drawing Sheet

PREPARATION OF ADIPIC ACID FROM LACTONES

FIELD OF THE INVENTION

This invention relates to the preparation of adipic acid by the reaction of certain lactones with carbon monoxide and water in the presence of a homogeneous rhodium catalyst and an iodide or bromide promoter.

BACKGROUND OF THE INVENTION

In U.S. Pat. Nos. 4,622,423 and 4,788,333, Burke discloses a two-step process for converting butadiene to adipic acid which gives high yields of this important diacid. The first step is the hydrocarboxylation of butadiene to form 3-pentenoic acid. The second step is the hydrocarboxylation of 3-pentenoic acid with carbon monoxide and water in the presence of a rhodium-containing catalyst, an iodide promoter and certain inert halocarbon solvents, e.g., methylene chloride.

It is disclosed in U.S. Pat. No. 4,788,333 that γ-valerolactone is a significant by-product in the hydrocarboxylation of butadiene. It has also been found that α-methyl-γ-butyrolactone is a minor (<1%) by-product of this reaction. Both γ-valerolactone and α-methyl-γ-butyrolactone are inert towards further carbonylation (or hydrocarboxylation) under the reaction conditions which are effective for the hydrocarboxylation of 3-pentenoic acid. Since these by-products represent a yield-loss, it would be useful to find a process for converting these lactones to adipic acid.

Japanese Published Pat. application, Sado et al., 92,913/1979 discloses the preparation of dicarboxylic acids, by reacting lactones and carbon monoxide in the presence of platinum group catalysts, with iodine compounds as promoters. In Example 3, γ-valerolactone is carbonylated in the presence of a rhodium catalyst to give the expected 2-methylglutaric acid in low yield (20.5%) and a smaller amount of the unbranched adipic acid (5.8%). It has now been found that certain branched lactones can be carbonylated to form substantial amounts of the unexpected, unbranched dicarboxylic acids.

SUMMARY OF THE INVENTION

This invention provides a process for the preparation of adipic acid which comprises: a) reacting at least one lactone selected from the group consisting of γ-valerolactone, α-methyl-γ-butyrolactone, αβ-dimethylpropiolactone, α-ethylpropiolactone and β-ethylpropiolactone with carbon monoxide and water in the presence of a homogeneous rhodium catalyst and at least one promoter selected from the group consisting of an iodide compound and a bromide compound at a temperature of about 190° C. to about 250° C. and at a carbon monoxide partial pressure of about 100 psi to about 2000 psi, wherein the mole ratio of promoter to rhodium is between about 1:1 and about 20:1, and wherein said temperature and pressure are within the polygon shown in the Figure; and b) quenching the reaction when the rate of carbon monoxide uptake declines sharply.

DETAILED DESCRIPTION OF THE INVENTION

Figure 1:
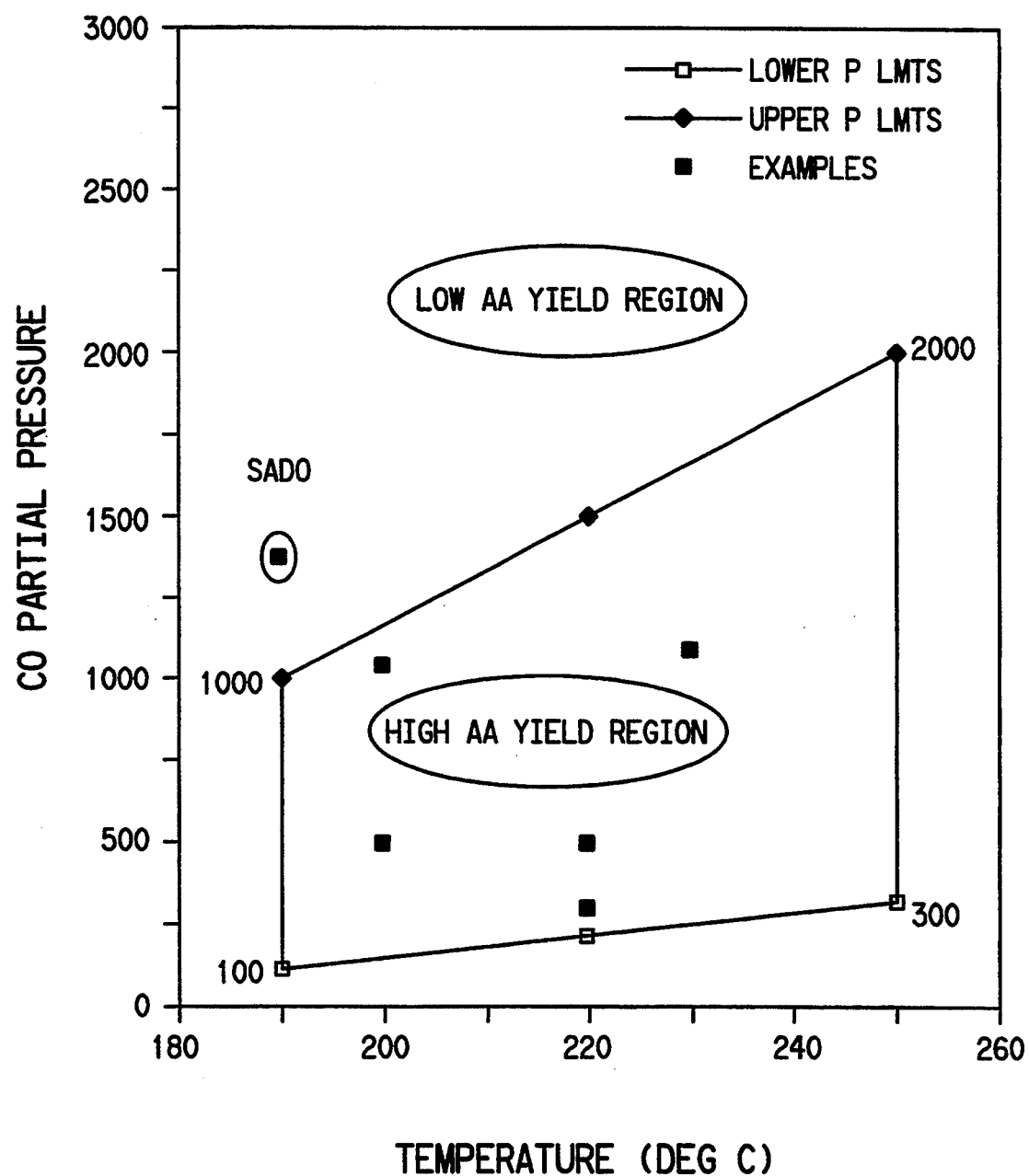
FIG. 1 is a graphic representation of the relationship between temperature and carbon monoxide partial pressure. The polygon shown on the graph is the area where high yields of adipic acid may be achieved from the rhodium-catalyzed hydrocarboxylation of γ-valerolactone, α-methyl-γ-butyrolactone, αβ-dimethylpropiolactone, α-ethylpropiolactone or β-ethylpropiolactone.

Although it has been shown by Sado and Tashima (JP 92,913/1979) that iodide-promoted rhodium catalysts can be used to carbonylate an alkyl-substituted lactone to form the corresponding linear dicarboxylic acid, the reported yield is very low. In particular, the yield of adipic acid from γ-valerolactone is only 5.8%.

It has now been found that, contrary to what is taught in the prior art, good yields of adipic acid can be obtained by the rhodium-catalyzed carbonylation of certain methyl- and ethyl-substituted lactones. This is achieved by carefully controlling a number of process variables. It is especially important to use the proper molar ratio of promoter to rhodium and to maintain the temperature and partial pressure of carbon monoxide in the reaction mixture within the limits of the polygon shown in the Figure.

It has also been found that the desired product, adipic acid, is slowly converted under the reaction conditions to branched acids (e.g., 2-methylglutaric acid) and reduced products (e.g., valetic acid). Therefore, in order to get the highest possible yields of adipic acid, it is usually necessary to quench the reaction before all of the lactone has reacted.

The γ-valerolactone or α-methyl-γ-butyrolactone used as the starting materials for the process of this invention may be obtained from the hydrocarboxylation reaction described in U.S. Pat. No. 4,788,333, or they may be obtained from any other source. The syntheses of αβ-dimethylpropiolactone, α-ethylpropiolactone and β-ethylpropiolactone have been described in the prior art.

The rhodium catalyst can be derived from any rhodium compound, or mixture of rhodium compounds, that is free of interfering ligands, such as bidentate phosphines and nitrogen ligands, and that is capable of forming a homogeneous solution under the reaction conditions. Suitable rhodium compounds include those described in U.S. Pat. No. 4,788,333, (col. 3, lines 37–54), as well as the bromide analogs of the rhodium iodide and rhodium chloride compounds listed in U.S. Pat. No. 4,788,333. The amount of rhodium in the reaction mixture should be between 0.1 parts and 10 parts per 1000 parts of the reaction mixture, preferably about 0.4 to about 1.7 part per 1000 parts. The weight of the reaction medium includes the weight of solvent, catalyst, promoter, and reactants. The rate of lactone carbonylation increases with increasing concentration of rhodium, but the rate of adipic acid decomposition may also increase.

The catalyst, which can be preformed or can be formed is situ, must be promoted to achieve a satisfactory reaction rate. Suitable promoters are iodide and bromide compounds, and mixtures thereof. Preferred iodide and bromide promoters include HI, HBr, lower alkyl bromides, and lower alkyl iodides, such as methyl bromide, bromoethane, 1-bromobutane, 1,4-dibromobutane, 2-bromopropane, 1-bromopropane, bromoheptane, methyl iodide, iodoethane, 1-iodobutane, 1,4-diiodobutane, 2-iodopropane, 1-iodopropane and iodoheptane. Most preferred are HI, HBr and methyl iodide. Surprisingly, linear selectivity is higher and reduction to saturated C5 acids is less when the promoter is HBr. The promoter and rhodium can be present in the same compound, as in rhodium iodide. Generally, the concentration of promoter is between 0.05–1.0% by weight based on the weight of the reaction mixture. In addition, the molar ratio of promoter to rhodium should be in the range of 1:1 to 20:1, preferably 2:1 to 15:1. At molar ratios greater than 0:1, the amount of adipic acid recovered is greatly diminished.

The lactones which are starting materials for this process are liquids at room temperature, and so the use of additional solvent is not essential. However, higher adipic acid yields and conversions are obtained in carboxylic acid solvents. The preferred solvents are acetic acid, valetic acid, and mixtures of carboxylic acids, such as those produced during the hydrocarboxylation of butadiene. Other suitable solvents are those which are stable under the highly acidic, high temperature conditions of the reaction. Other suitable solvents include saturated chlorinated solvents such as methylene chloride; carboxylic acids having 1–10 carbon atoms; aromatic compounds such as toluene, xylene and chlorobenzene; and polar aprotic solvents such as tetramethylene sulfone. Mixtures of solvents can also be used. If a solvent is used, it will usually be present in about 10 to about 90 percent by weight of the reaction mixture.

The operable limits of temperature and partial carbon monoxide pressure are interrelated. For example, at fixed CO partial pressure, selectivity in the conversion of $\gamma$-valerolactone to adipic acid vs. branched acids increases with temperature. Similarly, at a given temperature, selectivity to adipic acid increases with decreasing CO partial pressure. Overall, the temperature range is about 190° C. to about 250° C. and the CO partial pressure range is 100 to 2000 psi at the temperature of the reaction, as shown in the FIG. 1. At lower temperatures the reaction is too slow, and at higher temperatures side-reactions, such as decarboxylation, are significant. The optimum temperature is between 200° C. and 240° C. The optimum CO partial pressure will depend on the temperature, higher pressures being required to stabilize the catalyst at high temperatures. At 220° C. to 240° C., the optimum CO pressure is 200–600 psi.

It is also important to quench the reaction when the rate of carbon monoxide uptake has declined sharply, or ceased altogether, because at this point the amount of lactone that is reacting is relatively small, and but other side reactions are continuing, and the side reactions will reduce the overall yield and selectivity. The reaction can be quenched in a number of ways, for example, by reducing the temperature to less than about 120 degrees.

Although water is necessary for the formation of adipic acid from the lactones, the amount of water present at any given time should be kept low, preferably less than one part per 20 parts by weight of solvent. If no solvent is used, then the amount of water should be less than about one part per 20 parts by weight of the reaction mixture. A stoichiometric amount of water may be added at the beginning of the reaction, but it is preferred that it be added continuously as consumed by the reaction to avoid undesirably high concentrations. The amount of water may exceed the stoichiometric amount, but should not be present in great excess.

The reaction time will depend on many of the process variables, including temperature and rhodium concentration. Typically, reaction times of 0.25 to 5 hours are sufficient to convert most of the lactone starting material to acid products. The progress of the reaction, and therefore the optimum time, can be determined by withdrawing samples from the reaction mixture and analyzing the samples by standard techniques, or by monitoring the uptake of carbon monoxide. A sharp drop in the rate of CO uptake signals a sharp decrease in the rate of lactone carbonylation, and hence in the rate of adipic acid formation. Further reaction at this point results in substantial conversion of the desired adipic acid to undesired side-products.

Isolation of the adipic acid can be accomplished in any of several standard procedures, including, but not limited to, filtration (when reaction mixture is a non-solvent for the adipic acid), solvent extraction, and chromatography.

The following examples are presented to illustrate but not to restrict the present invention. Parts and percentages are by mole % and the products were analyzed by gas chromatography as the methyl esters unless otherwise noted.

EXAMPLES

Example 1

Conversion of $\gamma$-Valerolactone to Adipic Acid using a Rhodium Catalyst and Hydrogen Bromide Promoter in Acetic Acid Solvent at 220° C. and 600 psi.

A 300 ml Hastelloy-C mechanically stirred autoclave was flushed with nitrogen and then with high purity carbon monoxide. It was then charged with 200 ml of an acetic acid solution containing 19.95 grams (200 mmole) of $\gamma$-valerolactone (VL), 10.77 grams 30% HBr in acetic acid (30 mmole HBr), and 6.65 grams o-dichlorobenzene (ODCB) (internal GC standard). The autoclave was pressured with carbon monoxide (CO) to 300 psi and then heated to 220° C. The reaction was initiated by injecting into the autoclave a solution made by dissolving 0.53 grams (2 mmoles) $RhCl_3.3H_2O$ in 2.26 grams (230 mmole) water. The autoclave pressure was then immediately adjusted to 600 psi with CO by means of a regulator valve. An additional 16 ml of water was added continuously over 2 hours via a high pressure syringe pump. The autoclave pressure was maintained constant at 600 psi by feeding CO from a reservoir at an initial pressure of 1200 psi. Carbonylation rate was measured by monitoring the reservoir pressure drop.

Uptake of CO ceased after about 75 minutes. Based on the initial (first 45 minute) CO uptake the initial first order rate constant for the reaction was $30 \times 10 - 3$ min $-1$. The reaction was allowed to run for a total of 2 hours after which it was cooled to 20° C. The excess CO was vented through a control valve and the product was discharged. The autoclave was washed first with 150 ml methanol at 100° C. under autogenous pressure and then with 100 ml methanol at room temperature.

The product and washes from the autoclave were combined, filtered and the filtrate was diluted to 500 ml with methanol. A sample of this solution, was esterified by heating in a sealed vial at 90° C. for 14 hours with excess methanol and p-toluenesulfonic acid esterification catalyst. It was analyzed as the methyl esters by capillary gas chromatography. The analysis showed the following composition (moles product per 100 moles VL charged:

|  | Actual | Normalized |
|---|---|---|
| Recovered $\gamma$-valerolactone | 19.8% | 20.6 |
| Adipic acid | 42.8% | 44.6 |
| 2-methylglutaric acid | 19.3% | 20.1 |

-continued

|  | Actual | Normalized |
|---|---|---|
| Ethylsuccinic acid | 3.8% | 3.9 |
| 2-pentenoic acid | 0.5% | 0.6 |
| valeric acid | 7.8% | 8.2 |
| 2-methylbutyric acid | 1.8% | 1.9 |
| Total | 96.0% | 100% |

Product accounting* was 96%, valerolactone conversion was 80.2% and adipic acid yield** was 53.4%.
*Moles of all products recovered divided by moles VL charged
**Moles of adipic acid formed per 100 moles VL reacted (uncorrected for accounting losses)

Example 2

Conversion of γ-Valerolactone to Adipic Acid using a Rhodium Catalyst and Hydrogen Bromide Promoter in Acetic Acid Solvent at 220° C. and 600 psi The experiment in Example 1 was repeated except that the amount of $RhCl_3.3H_2O$ catalyst was increased to 1.06 g (4.0 mmoles). Uptake of CO ceased after about 60 minutes. The initial first order rate constant for the reaction was $46.2 \times 10^{-3}$ min $^{-1}$ (This represents a half life of about 15 minutes). GC analysis of the product showed 86.9% VL conversion and the following normalized yields: Adipic acid (AA) 27.4%, methyl glutaric acid (MGA) 30.3, ethylsuccinic acid (ESA) 8.5, valetic acid (VA) 16.8. Linearity is 41.4%

Example 3

Conversion of y-Valerolactone to Adipic Acid using a Rhodium Catalyst and Hydrogen Bromide Promoter in Acetic Acid Solvent at 220° C. and 400 psi.

The experiment in Example 1 was repeated except that the initial cold pressure was 150 psi, the final total pressure at temperature was 400 psi, the total volume of solution was 150 ml, and the amounts of the other components in the solution were: γ-valerolactone 15.0 g (150 mmoles), 30% HBr in acetic acid 8.1 g (30 mmoles), ODCB 5.0 g, $RhCl_3 .3H_2O$ 0.8 g (3 mmoles) and water 3.1 g (172.5 mmoles).

CO uptake ceased after about 3 hours. The initial (first 60 minute) first order rate constant for the reaction was $5.8 \times 10^{-3}$ min $^{-1}$. The reaction was allowed to run for a total of 4 hours. GC analysis of the product showed 63.5% VL conversion, 101.9% analytical product accounting and the following normalized yields: AA 60.5%, MGA 20.8%, ESA 4.0%, VA 12.2%.

Example 4

Conversion of γ-Valerolactone to Adipic Acid using a Rhodium Catalyst and Hydrogen Iodide Promoter in Acetic Acid Solvent at 200° C. and 600 psi.

The experiment in Example 1 was repeated except that the hydrogen bromide was replaced with 4.5 g 57% aqueous HI (20 mmoles HI) and the Rhodium catalyst was [Rh(COD)Cl]2 (0.49 g; 2.0 mmoles). The reaction was allowed to proceed for 5 hours at which time CO uptake had ceased. The first order rate constant for the reaction was $13.0 \times 10^{-3}$ min $^{-1}$. GC analysis showed 78.1% VL conversion and the following normalized yields: AA 41.2%, MGA 33.6%, ESA 6.3%, VA 15.6%. Linearity is 51.4%.

Example 5

Conversion of γ-Valerolactone to Adipic Acid using a Rhodium Catalyst and Methyl Iodide Promoter in Acetic Acid Solvent at 200° C. and 600 psi.

The experiment in Example 1 was repeated except that the hydrogen bromide was replaced with 2.13 g (15 mmoles) methyl iodide and 0.96 g methanol and the amount of rhodium catalyst was 0.4 g (1.5 mmoles). The amount of solvent was also reduced to 150 ml and the amounts of VL and water, and ODCB were correspondingly reduced by 25%. The reaction was allowed to proceed for 5 hours at which time CO uptake had ceased. The first order rate constant for the reaction was $18.0 \times 10^{-3}$ min $^{-1}$. GC analysis showed 86.8% VL conversion and the following normalized yields: AA 43.4%, MGA 33.3%, ESA 7.3%, VA 9.5%. Linearity is 51.7%.

Example 6

Hydrocarboxylation of alpha-Methylbutyrolactone with Rh Catalyst and HI Promoter in Acetic Acid Solvent at 200° C. and 1160 psi.

A 300 ml glass lined Hastelloy-C shaker tube was charged with 45 ml of glacial acetic acid, 4.0 grams (40 mmoles) of alpha-methylbutyrolactone (MBL), 0.6 g 57% aqueous HI (2.7 mmoles HI), 1.4 g (80 mmoles) water and 0.21 g (0.8 mmole) $RhCl_3.3H_2O$.

The tube was closed, cooled to −78° C. evacuated and then pressured with carbon monoxide to 500 psi. The tube was heated with agitation to 200° C. over about 45 minutes; the pressure at 200° C. was about 1160 psi (CO partial pressure was about 1060 psi). The temperature was maintained at 200° C. and additional 2 hours and CO was added at 15 minute intervals to maintain the total pressures constant at about 1160 psi. The reaction was terminated after 2 hours by cooling to 0° C. The excess CO pressure was slowly vented, the product was discharged and the tube was rinsed with two 20 ml portions of methanol.

The product and washings were combined and the solution was filtered. Internal standard (5.00 g ODCB) was added and the solution was made up to 200 ml with methanol. The sample was esterified as described in Example 1 and it was analyzed as the methyl esters on a 30 m ×0.25 mm CP-SIL-8 CB capillary GC column.

The analysis showed 100% MBL conversion, 98% product accounting and the following normalized yields: 25.5% AA, 51.4% branched diacids (40.8% MGA, 5.9% ESA, 4.7% 2,3-dimethylsuccinic acids, DMSA) and 18.0% valetic + 2-methylbutyric acids. The linearity is 33.2%.

Example 7

When the above reaction was repeated at 230° C. at a total pressure of 1180–1200 psi the following results were obtained: 100% MBL conversion, 94% product accounting and the following normalized yields: 15.3% AA, 40.8% branched diacids (28.9% MGA, 6.4% ESA, 5.5% DMSA) and 29.9% valeric +2-methylbutyric acids. The linearity was 27.3%.

I claim:

1. A process for the preparation of adipic acid which comprises:
   a) reacting at least one lactone selected from the group consisting of γ-valerolactone, α-methyl-γ-butyrolactone, αβ-dimethylpropiolactone, α-ethylpropiolactone and β-ethylpropiolactone with carbon monoxide and water in the presence of a homogeneous rhodium catalyst and at least one promoter selected from the group consisting of an iodide compound and a bromide compound at a temperature of about 190° C. to about 250° C. and at a carbon monoxide partial pressure of about 100 psi to about 2000 psi, wherein the mole ratio of promoter to rhodium is between about 1:1 and about 20:1; and wherein said temperature and pressure are within the polygon shown in the Figure; and b) quenching the reaction when the rate of carbon monoxide uptake declines sharply.

2. The process of claim 1 in which the reaction is carried out in a solvent, and the amount of water present in the reaction mixture is not more than about 1 part of water per 20 parts of solvent.

3. The process of claim 2 in which the solvent is at least one member selected from the group consisting of methylene chloride, carboxylic acids having 1 to 10 carbon atoms, toluene, xylene, and tetramethylene sulfone.

4. The process of claim 3 in which the solvent is acetic acid.

5. The process of claim 1 in which the promoter is selected from the group consisting of HI, HBr, lower alkyl iodide, and lower alkyl bromide.

6. The process of claim 5 in which the ratio of promoter to rhodium is in the range of 2:1 to 15:1.

7. The process of claim 6 in which the promoter is HBr.

8. The process of claim 1 in which the homogeneous rhodium catalyst is present in a ratio of between 0.1 and 10 parts of rhodium per 1000 parts of the reaction mixture.

9. The process of claim 8 in which the homogeneous rhodium catalyst is present in a ratio of between 0.4 and 1.7 parts of rhodium per 1000 parts of the reaction mixture.

10. The process of claim 1 in which the promoter is hydrogen iodide, or a lower alkyl iodide, and the ratio of promoter to rhodium is in the range of 2:1 to 15:1.

11. The process of claim 1 is which the lactone is $\gamma$-valerolactone.

12. The process of claim 1 in which the lactone is $\alpha$-methyl-$\gamma$-butyrolactone.

13. The process of claim 1 in which the lactone is a mixture of at least two lactones selected from the group consisting of $\gamma$-valerolactone, $\alpha$-methyl-$\gamma$-butyrolactone, $\alpha\beta$-dimethylpropiolactone, $\alpha$-ethylpropiolactone and $\beta$-ethylpropiolactone.

14. The process of claim 2 in which the solvent is a mixture of carboxylic acids having 1 to 10 carbon atoms.

* * * * *